(12) United States Patent
Gibson-Horn

(10) Patent No.: US 10,583,028 B2
(45) Date of Patent: *Mar. 10, 2020

(54) METHODS FOR WEIGHTING GARMENTS OR ORTHOTICS AND GARMENTS AND ORTHOTICS THEREFOR

(75) Inventor: Cynthia Gibson-Horn, Oakland, CA (US)

(73) Assignee: Motion Therapeutics, Inc., Oakland, CA (US)

( * ) Notice: Subject to any disclaimer, the term of this patent is extended or adjusted under 35 U.S.C. 154(b) by 839 days.

This patent is subject to a terminal disclaimer.

(21) Appl. No.: 12/728,873

(22) Filed: Mar. 22, 2010

(65) Prior Publication Data
US 2010/0248915 A1 Sep. 30, 2010

Related U.S. Application Data

(63) Continuation of application No. 11/565,207, filed on Nov. 30, 2006, now Pat. No. 7,708,673, which is a
(Continued)

(51) Int. Cl.
*A61F 5/02* (2006.01)
*A63B 21/065* (2006.01)

(52) U.S. Cl.
CPC .............. *A61F 5/02* (2013.01); *A63B 21/065* (2013.01); *A63B 2208/12* (2013.01)

(58) Field of Classification Search
CPC .. A63B 21/00134; A63B 21/00138–21/00152; A63B 21/065; A61F 5/02
(Continued)

(56) References Cited

U.S. PATENT DOCUMENTS

| 4,122,840 A | 10/1978 | Tsuchiya et al. |
| 4,268,917 A | 5/1981 | Massey |

(Continued)

FOREIGN PATENT DOCUMENTS

| GB | 2129281 | 5/1984 |
| SE | 218063 | 1/1968 |

(Continued)

OTHER PUBLICATIONS

Anonymous (2002). "Full Catalog with Pictures and Descriptions," Online! Spinal Technologies located at http:/www.spinal-Tech.com/order/Catalog2002.pdf.
(Continued)

*Primary Examiner* — Jennifer Robertson
(74) *Attorney, Agent, or Firm* — Shay Glenn LLP

(57) ABSTRACT

Methods and apparatuses for aligning a person's center of gravity over the base of support using a weighted garment or orthotic are herein provided. These methods and apparatuses are particularly suited to individuals suffering from various balance or neurological disorders. The methods described herein involve the use of body positioning and perturbation techniques. These methods may be manual, computer assisted, or some combination thereof. In some variations, video recording equipment or other electronic equipment is used. The apparatuses of the present invention comprise a variety of weighted garments or orthotics. These garments or orthotics may take on any number of configurations. In some variations, the weighted garment or orthotic is a vest, in other variations, the weighted garment or orthotic is a brassiere, corset, shoulder pad, undergarment, belt, seating device to be used in combination with a wheelchair, tee shirt, body suit, or combinations thereof.

2 Claims, 6 Drawing Sheets

Related U.S. Application Data continuation of application No. 10/353,539, filed on Jan. 28, 2003, now Pat. No. 7,156,792.

(58) Field of Classification Search
USPC .......................... 482/105, 93; 2/102; 600/592
See application file for complete search history.

(56) References Cited

U.S. PATENT DOCUMENTS

| | | | |
|---|---|---|---|
| 4,382,302 A * | 5/1983 | Watson | 2/102 |
| 4,384,369 A * | 5/1983 | Prince | A63B 21/065 2/227 |
| 4,562,464 A | 12/1985 | Kurihara | |
| 4,602,387 A | 7/1986 | Zakrzewski | |
| 4,658,442 A | 4/1987 | Tomlinson et al. | |
| 4,738,269 A | 4/1988 | Nashner | |
| 4,823,778 A * | 4/1989 | Ewing | 606/204.35 |
| 4,971,073 A | 11/1990 | Schneider | |
| 4,989,267 A * | 2/1991 | Watson | 2/102 |
| 5,002,270 A | 3/1991 | Shine | |
| 5,052,406 A | 10/1991 | Nashner | |
| 5,067,484 A | 11/1991 | Hiemstra-Paez | |
| 5,120,288 A * | 6/1992 | Sinaki | 482/105 |
| 5,144,694 A | 9/1992 | Conrad Da oud et al. | |
| 5,209,240 A | 5/1993 | Jain et al. | |
| 5,388,591 A | 2/1995 | De Luca et al. | |
| 5,476,103 A | 12/1995 | Nahsner | |
| 5,582,583 A | 12/1996 | Ballantyne | |
| 5,659,898 A | 8/1997 | Bell, Jr. | |
| 5,713,840 A | 2/1998 | Brentham | |
| 5,799,328 A | 9/1998 | Harlem et al. | |
| 5,810,699 A | 9/1998 | Nadeau | |
| 5,937,441 A * | 8/1999 | Raines | 2/69 |
| 5,943,700 A | 8/1999 | Hammer et al. | |
| 5,951,446 A | 9/1999 | Monforte | |
| 5,957,873 A | 9/1999 | Allen | |
| 5,978,964 A | 11/1999 | Gaston | |
| 6,005,041 A | 12/1999 | Cook | |
| 6,010,465 A | 1/2000 | Nashner | |
| 6,056,671 A | 5/2000 | Marmer | |
| 6,056,674 A | 5/2000 | Cook | |
| 6,081,924 A | 7/2000 | Ott | |
| 6,113,521 A * | 9/2000 | Winston | 482/105 |
| 6,200,243 B1 * | 3/2001 | Meranto | 482/105 |
| 6,200,244 B1 * | 3/2001 | Cook | 482/105 |
| 6,209,135 B1 * | 4/2001 | Irvin | 2/102 |
| 6,244,997 B1 | 6/2001 | Cook | |
| 6,248,043 B1 * | 6/2001 | Morton | 482/11 |
| 6,314,580 B1 | 11/2001 | Greenberg et al. | |
| 6,364,851 B1 | 4/2002 | Nafpliotis | |
| 6,554,752 B2 * | 4/2003 | Cook | 482/105 |
| 6,557,176 B2 * | 5/2003 | Franco-Sion | 2/102 |
| 6,671,887 B1 * | 1/2004 | Eligan et al. | 2/228 |
| 6,692,413 B1 * | 2/2004 | Greenberg | A41D 13/0012 2/108 |
| 6,788,968 B2 | 9/2004 | Pettibon | |
| 2002/0169376 A1 | 11/2002 | Pettibon | |
| 2006/0000478 A1 | 1/2006 | Taylor | |

FOREIGN PATENT DOCUMENTS

| | | |
|---|---|---|
| WO | WO-98/47450 | 10/1998 |
| WO | WO-2004/066821 | 8/2004 |

OTHER PUBLICATIONS

Bastian, A.J. (Jun. 1997), "Mechanisms of Ataxia," Phys. Ther. 77(6):672-675.

Chase, R.A. et al. (May 1, 1965), "Modification of Intention Tremor in Man," Nature 206(4983): 485-487.

Clopton, N. et al. (Mar. 2003), "Effects of Axial Weight Loading on Gait for Subjects with Cerebellar Ataxia: Preliminary Findings," Neurology Report 27(1): 15-21.

Frank, J.S. and Earl, M. (1990), "Coordination of Posture and Movement," Physical Therapy 70(12):855-863.

Gillen, G. (Jan./Feb. 2000), "Improving Activities of Daily Living Performance in an Adult with Ataxia," The American Journal of Occupational Therapy 54(1):89-96.

Hewer, R.L. et al. (1972), "An Investigation into the Value of Treating Intention Tremor by Weighting the Affected Limb," Brain 95(Part IV):579-590.

Holmes, G. (Mar. 1939), "The Cerebellum of Man," Brain 62(1):1-30.

Horn, C.G. et al. (Aug. 2003), "Post Lower Extremity Fracture Study," Journal of Bone and Mineral Research 18(Suppl. 1):S278.

International Search Report dated Aug. 6, 2004, for PCT Patent Application No. PCT/US2004/002255 filed on Jan. 25, 2004, eight pages.

Morgan, M.H. et al. (1975), "Application of an Objective Method of Assessing Intention Tremor—A Further Study on the Use of Weights to Reduce Intention Tremor," Journal of Neurology Neurosurgery and Psychiatry 38:259-264.

Nashner, L. (1990), "Sensory, Neuromuscular and Biomechanical Contributions to Human Balance," Proceedings of the APTA Forum in Nashville, TN, American Physical Therapy Association: Alexandria, VA, pp. 5-12.

NeuroCom International, Inc. (1998), "Assessment of Balance and Mobility Functions: A Reference Population Study Based on the Balance Master 6.1," NeuroCom International, Inc., Clackamas, OR, pp. 1-31.

O'Sullivan, S.B. (2001), "Multiple Sclerosis," Chapter 22 in *Physical Rehabilitation: Assessment and Treatment*, O'Sullivan, S.B. et al., eds., Fourth Edition, F.A. Davis Company, Philadelphia, PA, pp. 715-741.

Schapiro, R.T., (1998), "*Symptom Management in Multiple Sclerosis*," Third Edition, Demos Medical Publishing Co., Inc., New York, NY, pp. ix-x (Table of Contents Only).

Snow, C.M. et al., (Sep. 2000), "Long-Term Exercise Using Weighted Vests Prevents Hip Bone Loss in Postmenopausal Women," Journal of Gerontology 55A(9):M489-M491.

Woollacott, M.H. and Tang, P.F., (1997), "Balance Control During Walking in the Older Adult: Research and its Implications," Physical Therapy 77(6):646-660.

Written Opinion dated Aug. 6, 2004, for PCT Patent Application No. PCT/US2004/002255 filed on Jan. 1, 2004, six pages.

\* cited by examiner

METHODS FOR WEIGHTING GARMENTS OR ORTHOTICS AND GARMENTS AND ORTHOTICS THEREFOR

PRIORITY

This application is a continuation of U.S. application Ser. No. 11/565,207, filed Nov. 30, 2006, which is a continuation of U.S. application Ser. No. 10/353,539, filed Jan. 28, 2003, now U.S. Pat. No. 7,156,792.

FIELD OF THE INVENTION

Described here are methods for providing a patient having a balance disorder, or proprioceptive loss, with a weighted garment or orthotic device tending to improve the patient's balance. Garments and other devices produced using these methods are also shown.

BACKGROUND OF THE INVENTION

Many individuals suffering from neurological disorders, balance dysfunction, difficulty with weight shifting, and loss of proprioception, have problems maintaining their center of gravity ("COG") over their base of support, the perimeter defining the contact region surrounding the feet. The inability to maintain one's COG over the base of support results in decreased postural and motor control in sitting, standing, changing positions, and locomotion. Maintenance of the COG over the base of support is desirable for smooth and coordinated movement in balance and gait.

The ability to maintain COG balance over the base of support relies in part on three input systems: the somatosensory (proprioceptive and tactile input from the torso, feet, and ankles); the vestibular (spatial orientation and balancing functioning); and the visual (input from sight). When a problem occurs in one of these input systems, it may affect both the input to the sensory integration system of the central nervous system ("CNS") and the resulting ability to use the remaining one or more of the somatosensory, vestibular, or visual input systems for balance. The CNS may then tend to rely more heavily on one input system relative to another, or even to rely on other areas of the nervous system itself.

The nervous system's reliance on other areas of the CNS to compensate for the deficiency of one input system can lead to nervous system fatigue. In addition, problems associated with ineffective or inaccurate input or output tend to affect motor control, speed, movement coordination, automatic postural reaction, ability to control one's COG over their base of support, weight shifting, and equal weight bearing. Alterations in input, central processing, and output systems vary with age, with the type and severity of the neurological problem, and with the severity of any resulting neurological degeneration.

Proper coordination of posture and movement rely on the body's ability to initiate and effect subtle postural adjustments. For example, one's ability to remain in an upright position while sitting or standing is fundamental to safe and efficient movement. Similarly, balance control while walking requires proactive control of upper body stability in both the sagittal and frontal planes, as well as the coordination of the upper and lower extremities. Such control is often compromised due to various neurological disorders. Correction of aberrant balance is often complicated by the biomechanics of certain movements.

For example, two thirds of a human's body weight is centered in the upper body (head, torso, and arms). When the body mass is not neutral, or is off-center, the center of gravity is not positioned over the base of support. This is simply a natural instability due to the anatomy of a human being. However, when a person cannot maintain control over this natural instability, decreased ability in function, coordination, balance and ambulation tend to occur. To ameliorate and/or eliminate this instability and facilitate better movement, I have found that providing certain counterbalances and proprioceptive cues to a person having such a problem tends to overcome upper body instability.

SUMMARY OF THE INVENTION

Provided herein are methods and devices for assisting a person having a balance disorder in need of such assistance, or for aligning a person's COG over their base of support biomechanically or proprioceptively (e.g., by receiving stimuli originating in muscles, tendons, and other internal tissues). Improvements in the ability to sit, stand, turn, walk, shift weight, coordinate, and balance may be achieved. The methods and apparatuses described here are suited to individuals suffering from various neurological disorders and orthopedic conditions. For example, persons suffering from cerebellar degeneration, Parkinson's disease, multiple sclerosis, age-related degenerative disorders, stroke, traumatic injury to the head, brain, or spinal cord, orthopedic injury, and cerebral palsy, may benefit from my described methods and apparatuses.

One described method provides an assessment of a patient's need for a selectively weighted garment or orthotic and for determining the proper weight placement within or upon the weighted garment or orthotic. These methods may be manual, e.g., observational, and/or to some degree computer assisted. Video recording equipment or other electronic equipment may be used.

For example, these methods may comprise the steps of observing a patient's ability to maintain their COG over their base of support, optionally perturbing the patient (e.g., by applying an external push or by having the patient try to resist the movement force, etc.) and observing their body's reaction to the perturbation, selectively weighting the patient's torso, and observing the patient's ability to maintain their COG over their base of support after being weighted. Additional steps may include temporarily reducing or eliminating the patient's vision and observing the patient's ability to maintain their COG over their base of support, and recording the position and value of each weight placed within the garment or orthotic. Any or all of the steps may be repeated as necessary. In addition, these methods may be computer assisted.

The present invention includes weighted garments or orthotics, typically produced using procedures described here. These garments or orthotics may take on any number of configurations. The garment or orthotic may be a vest, perhaps having at least one pocket for receiving and securing a weight therein, or may have a plurality of pockets. The pockets may be distributed throughout the vest in a plurality of orientations and have a plurality of sizes. The weighted garment or orthotic may also be a brassiere, corset, shoulder pad, belt, seating device to be used in combination with a wheelchair, tee shirt, body suit, undergarment, or combination thereof. Functionally, the weighted garments are of a form, size, shape, and thickness, suitable for correcting, assisting in or alleviating at least a portion of a patient's balance dysfunction.

The garment or orthotic may have pockets, receptacles, or tubes for placement of weights therein or thereupon. The garment or orthotic may be weighted in a distribution pattern determined by the methods of the present invention, or the material making up the garment or orthotic may be the weighted medium.

One garment of particular utility is a coat, vest, or shirt constructed in such a way that it has a number of elastic tubes situated along the body when worn. The tubes themselves may have openings at each end and at points intermediate in the tubes for introduction of weights at various portions within the tubes. Other garments of interest include undergarments such as brassieres, corsets, shoulder pads, belts, seating devices and the like that, if desired, may be used in combination with a wheelchair, tee shirts, undergarments, body suits, and combinations thereof.

DETAILED DESCRIPTION

Figure 1:
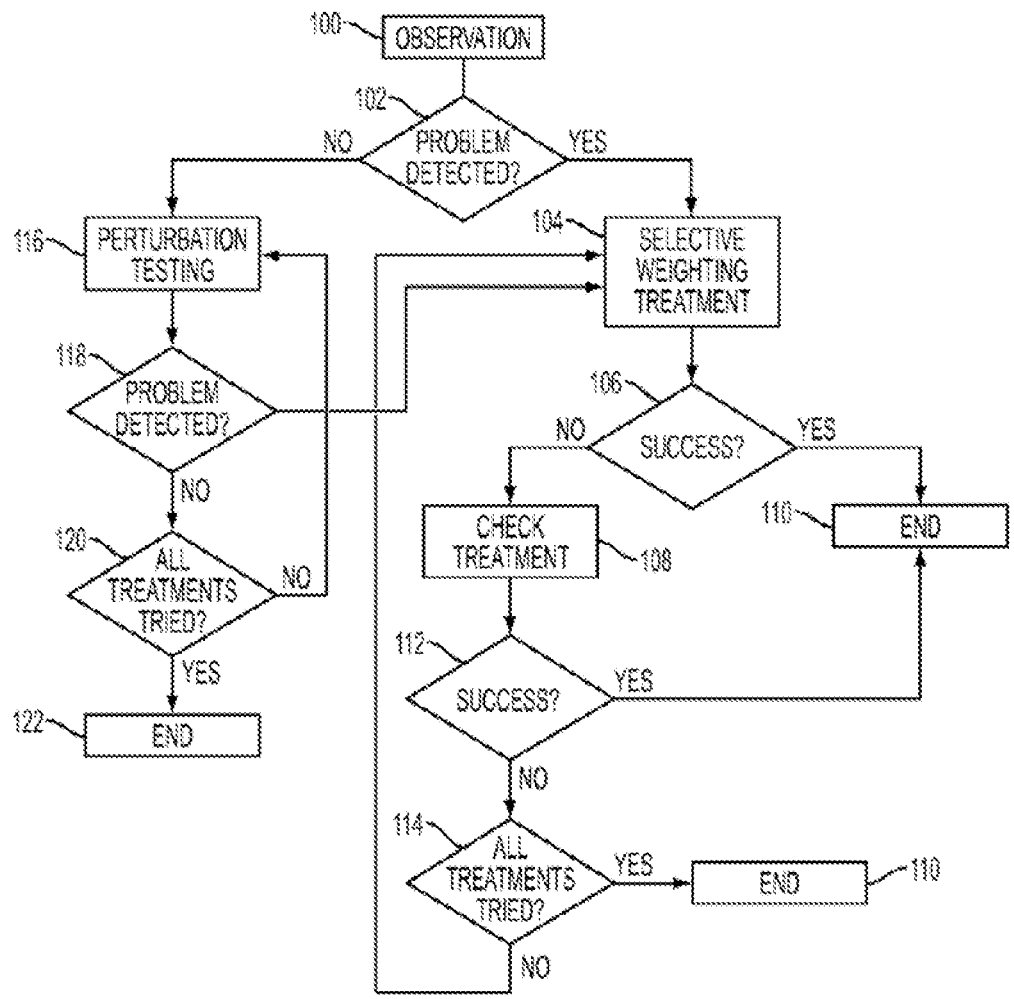
FIG. 1 provides a general flowchart of a method of weighting a garment or orthotic to improve a user's balance.

Described below are methods for assessing a need for a weighted garment or orthotic and for determining appropriate weight and weight placement within the garment or orthotic. These methods may variously be manual, computer assisted, or combinations of the two. Making reference now to the drawings, shown in FIG. 1 is a general overview of a method for assessing a need for a weighted garment or orthotic and for determining an appropriate weight and weight placement within that garment or orthotic.

In general, these methods make use of body positioning and perturbation techniques to detect balance dysfunction. When a balance dysfunction is identified, the method of the present invention may be used to systematically and selectively apply weight to the patient's torso. In general, a weight is selected for placement within the therapeutic garment or orthotic. The size may depend on, inter alia, the patient's tolerance for the weight and their treatment needs. Typically, the various weights applied to the garment range from ¼ pound to 5 pounds for adults, or less than that for children, for example, 1-3% of a patient's body weight. The determination of the appropriate weight may further be dependent upon on the patient's size, strength, and resistance to move the patient's COG to the center of the base of support.

In accordance with the methods described herein, continued perturbation and balance testing is done until the patient resists the perturbation or shows improvement in control or movement compared to the initial observations, or (ideally) evidences improvement in control and movement that cannot be further maximized. After an appropriate weight placement has been determined, changes in movement control and walking ability may be assessed. The patient may, during the procedure, be asked about their ability to tolerate additional weight and their overall comfort level with the weighted apparatus. In this way, the weight may be modified prior to the final preparation of the weighted apparatus if necessary.

First of all, in its most elemental form, this procedure is observational and heuristic. This procedure does not necessarily rely on specific balance standards for assessing the magnitude of a patient's balance dysfunction (e.g., Berg balance standards, Tinetti balance standards, posturography, etc.). The assessment of a patient's improvement during this described procedure is by observation following the various instructions given here, or may be had by monitoring a patient's COG placement after introduction of a specific weight at a specific site and comparing it to a comparable COG before that treatment step. Depending upon the malady and the patient, the appropriate treatment may result in placement of a weight on the side of the patient considered likely to move the COG further to a position of greater stability, biomechanically or proprioceptively.

As shown in FIG. 1, the first step 100 is an initial observation of the patient. In this step the patient's physical orientation is observed. This usually involves observation of the patient while sitting or standing, while the provider observes the patient's frontal and sagittal plane orientation, as well as bodily movements and balance dysfunction cues. The sagittal plane refers to the imaginary vertical plane through the body that divides the body into equal left and right halves. The frontal, or coronal plane, refers to the imaginary plane through the body that separates the front from the back.

For example, during observation, the patient may first be observed in a sitting orientation. The observation may involve the exploration of following questions: 1) is the patient able to sit upright without support?; 2) if the patient is unable to sit upright without support, which way does the patient tend to fall or lean?; 3) is the patient sitting with their body positioned in the midline of the coronal and sagittal planes?; 4) which way does the patient lean?; 5) what happens to the patient when they close their eyes (e.g., do they lean in a different direction, sway more, etc.)? If the patient is unable to sit without support for example, or there are other indications or cues that the patient has a balance dysfunction, the selective weighting process 104 may begin.

The patient may also be observed in a standing orientation. For example, the observation may involve the exploration of the following questions: 1) how does the patient get from the sitting to the standing positions (e.g., is this movement smooth; do they use their hands, etc)?; 2) can the patient stand without use of their hands?; 3) how many attempts does it take the patient to stand?; 4) how stable is the patient's initial standing balance (e.g., do they sway; how far apart are the patient's feet, etc.)?; 5) can the patient stand with feet together without falling?; 6) how many steps does it take for the patient to bring the feet together?; 7) does the patient falter while standing?; 8) what happens to the patient when they close their eyes (e.g., do they lean in a different direction, sway more, etc.). If the patient is unable to stand without support for example, or there are other indications or cues that the patient has a balance dysfunction, the selective weighting process 104 may begin.

The observation step 100 may also include observation of gait. For example, observation of gait may involve the exploration of the following questions: 1) is there a disturbance in the swing or stance phases of gait?; 2) does the patient have equal stride lengths?; 3) is there any hyperextension at the knee?; 4) does the patient scuff their foot while they walk?; 5) can the patient walk a strait line?; 6) does the patient loose their balance while walking (e.g., while walking straight, forward, or turning, etc.)?

In general, the observation may take any number of forms and includes all methods of observation useful in acquiring data. For example, the observation step may take the form of visual observation and may include the use of mechanical or electronic aids. Video recording equipment may be used to aid in observation step 100. In addition, it is often useful to first offset the patient's balance by physical perturbation during the observation step 100. Such perturbation may, for example, include applying one or more slight external forces to the patient, perhaps from a number of different directions. This type of perturbation testing is analogous to the perturbation testing done in step 116 and will be discussed in greater detail below.

That is, if after initial observation, no problem has been detected 102, perturbation step 116 may be performed. The detection of a problem 102 is based in large part on the observation of the patient's orientation and exploration of the questions highlighted above (or similar such questions). Perturbation step 116 may occur while the patient is in any given position (e.g., sitting or standing) and any number or types of perturbation forces may be applied to the patient.

For example, an anterior posterior perturbation force may be applied to the patient, wherein the patient receives a horizontal force to the sternum in a posterior direction. If the patient falls or leans backwards, this is termed a "posterior balance dysfunction." Similarly, a posterior anterior perturbation force may be applied to the patient, wherein the patient is pulled forward horizontally by both hands. If the patient falls or leans forward, this is termed an "anterior balance dysfunction." The patient may also be subjected to a lateral perturbation, wherein a force is directed laterally through the humerus at the top of the shoulder joint to displace the patient sideways, to the right or the left. If the patient falls or is unable to resist the perturbation, this is termed a "lateral dysfunction." Each of these dysfunctions may further be classified as "to the right" or "to the left" based on the direction the patient is unable to resist the perturbation.

The patient may also be subjected to a rotational perturbation. In a right rotational perturbation, the right shoulder of the patient is pulled forward and the left shoulder is pushed back. Similarly, in a left rotational perturbation, the left shoulder of the patient is pulled forward and the right shoulder of the patient is pulled back. If the patient exhibits less control over their right shoulder being pulled forward than their left shoulder, this is termed a "right rotation dysfunction." Conversely, if the patient exhibits less control over their left shoulder being pulled forward than their right shoulder, this is termed a "left rotation dysfunction."

However, as mentioned above, if during observation 100, a problem is detected 102, selective weighting treatment 104 may begin. The selective weighting step 104 involves the placement of individual weights on the torso to aid the patient in counteracting the displacement of COG over the base of support via biomechanical or proprioceptive input. At this stage, any method may be used to place the weights on the patient's torso. For example, the patient may be provided with a vest or other garment, or the weights may be placed on the patient's torso through any other method.

If a vest is used, for example, the vest may contain a number of pockets or receptacles for receiving weights. The vest may contain a plurality of pockets, having various sizes and orientations. In this way, weight placement along the torso's superior, posterior, lateral, or anterior directions, or any combinations thereof, may be assessed.

The weights may be flexible or rigid, and have any given thickness. The garment may be marked on the pockets or receptacles for recordation of the weight placement. For example, the pockets or receptacles may be numbered, or may be designated with alphabetic characters, symbols, pictures, figures, or any combinations thereof. Specifically, the pockets of the vest may be numbered and the method of weighting the orthotic identified and results recorded using a numbering system.

Figure 2A:
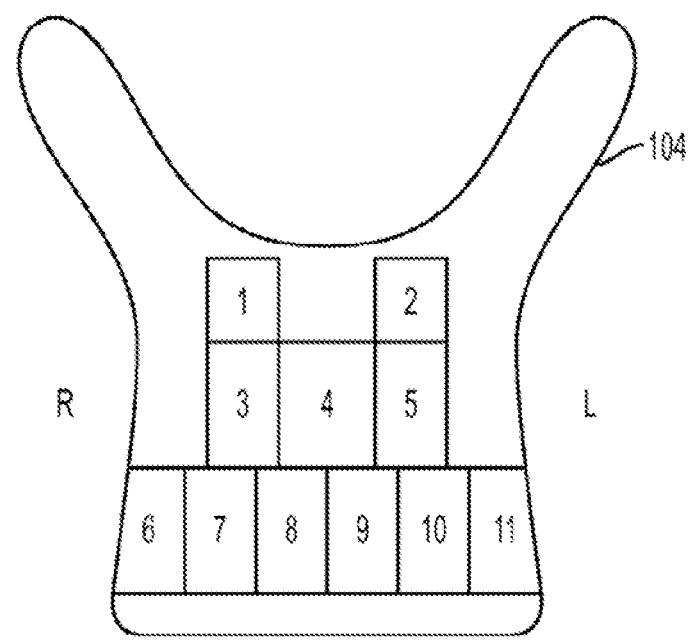
FIGS. 2A and 2B provide front and back panel views, respectively, of an illustrative vest that may serve as a weighted garment or orthotic.
Figure 2B:
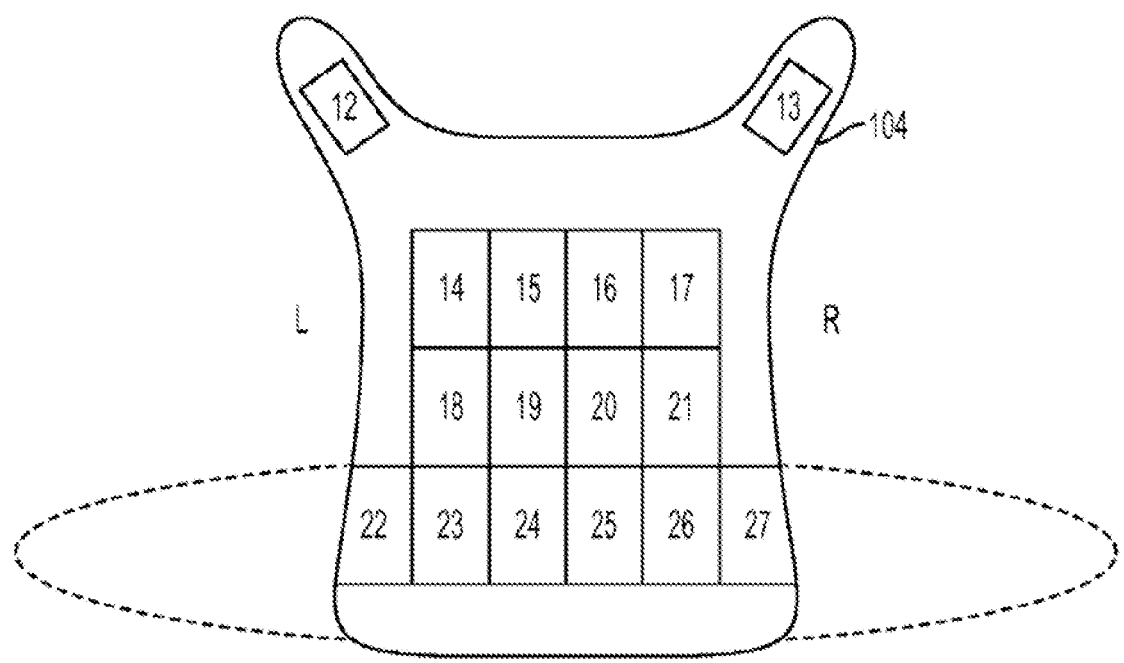

The method of weighting the patient or the orthotic is often dependent on the specific type of patient dysfunction identified during observation step 100 and perturbation testing 116. Reference will now be made to FIGS. 2A and 2B, wherein front and back views of a vest are respectively indicated. Again, this vest is a garment that itself may be used either as an end product (i.e., a garment to be worn by the patient) or as a tool to determine the placement and size of weights to be introduced into another garment, perhaps having greater aesthetic appeal. Other test garments may be used in the same way. For instance, it is my intent that test garments having the functional ability to hold weight in a single position during, for example, perturbation and balance testing, are included as garments suitable as test garments. For instance, an illustrative garment for testing may comprise, rather than a collection of pockets for inclusion of weights, a tacky exterior or an exterior having Velcro, or another method capable of holding a weight (i.e., 204) in position. The right side of the vest, while worn by the patient, is indicated with an R. Similarly, the left side of the vest, while worn by the patient, is indicated with an L.

Illustrated below are examples of how a vest may be selectively weighted.

Posterior Balance Dysfunction.

To test for appropriate weight placement with this dysfunction, a series of weights from ¼ to ½ pounds may be placed within any of pockets 1-11 until the desired weight shift or perturbation resistance is achieved. Pockets 1-11 are on the front of vest 104. Placement of weight may begin with pocket 4 and continue progressively to pockets 8 and 9 if determined necessary. Directionally, I have found that beginning the testing sequence in the middle of the vest, e.g., pocket 4, progressing downward to pockets 8 and 9, and then to the left and right pockets is a practical progression for this balance disorder. Additional pocket combinations may then be added until the desired weight shift or perturbation resistance is obtained. The desired amount of weight shift or perturbation resistance will be that amount resulting in an acceptable level of improvement in balance or movement from the baseline observation and perturbation steps. Once the desired weight shift or perturbation resistance is obtained, the weight placement (e.g., the amount of weight placed within each pocket and the corresponding weight-pocket location) may be recorded.

Posterior Lateral Balance Dysfunction to the Left.

For this malady, a series of weights from ¼ to ½ pounds may be placed within any of pockets 13, 1, 3, 4, 6, 7, or 8 and combinations thereof until the desired weight shift or perturbation resistance is achieved. Directionally, I have found that initially placing the weights higher on the body, and then adding or subtracting them lower on the body, is a practical progression for this malady. The desired amount of weight shift or perturbation resistance will be that amount resulting in an acceptable level of improvement in balance or movement from the baseline observation and perturbation steps. Patients having greater lateral instability than posterior instability occasionally may need a weight placed in a posterior right pocket (e.g., 17, 21, 26, or 27) as well as a weight placed in the front. Once the desired weight shift or perturbation resistance is obtained, the weight placement (e.g., the amount of weight placed within each pocket and the corresponding weight-pocket location) may be recorded.

Posterior Lateral Balance Dysfunction to the Right.

To test for appropriate weight placement with this dysfunction, a series of weights may be placed on the anterior left side of the patient with the occasional placement in one pocket in the posterior left side of the patient when the patient has more lateral dysfunction than posterior dysfunction. For example, from ¼ to ½ pounds of weight may be placed within any of pockets 12, 2, 4, 5, 9, 10, or 11, and combinations thereof until the desired weight shift or perturbation resistance is achieved. The desired amount of weight shift or perturbation resistance will be that amount resulting in an acceptable level of improvement in balance and movement from the baseline observation and perturbation steps. Once the desired weight shift or perturbation resistance is obtained, the weight placement (e.g., the amount of weight placed within each pocket and the corresponding weight-pocket location) may be recorded.

Lateral Balance Dysfunction to the Left.

I have found that even posterior anterior distribution of weights produces the best result unless the patient has a minor rotation, or decreased resistance or loss of neutral. To test for the appropriate weight placement for this dysfunction then, a series of weights from ¼ to ½ pounds may be placed within any of pockets 13, 1, 3, 6, 7, 8, 20, 21, 25, 26 or 27, and combinations thereof until the desired weight shift or perturbation resistance is achieved. The desired amount of weight shift or perturbation resistance will be that amount resulting in an acceptable level of improvement in balance and movement from the baseline observation and perturbation steps. To provide even weight distribution between the front and back segments of the weighting apparatus, weight may be placed within pockets 3 and 21, or within pocket 6 or 7 counterbalanced by weight placement within pockets 26 and 27 respectively. In some instances it may also be desirable to place a ½ pound weight at the shoulder, for example within pocket 13. Once the desired weight shift or perturbation resistance is obtained, the weight placement (e.g., the amount of weight placed within each pocket and the corresponding weight-pocket location) may be recorded.

Lateral Balance Dysfunction to the Right.

To test for the appropriate weight placement for this dysfunction, a series of weights from ¼ to ½ pound of weight may be placed within any of pockets 12, 2, 5, 9, 10, 11, 14, 15, 18, 19, 22, 23, or 24 and combinations thereof until the desired weight shift or perturbation resistance is achieved. These pockets are on the front and back of vest 104. The desired amount of weight shift or perturbation resistance will be that amount resulting in an acceptable level of improvement in balance and movement from the baseline observation and perturbation steps. I have found that beginning weighting on the upper, left, front, side of vest 104, proceeding down the front of the vest, proceeding to weight the upper left side of the back of the vest, and then proceeding down the back of the vest is a practical progression for this dysfunction. In some instances, it may be desirable to provide even weight distribution between the front and back segments of the weighting apparatus. In these instances, weight may be placed within pocket 5 counterbalanced by weight placement within pocket 19. Similarly weight may be placed within pockets 10 or 11 counterbalanced by weight placement within pockets 22 and 23 respectively. In some instances it may also be desirable to place a ½ pound weight at the shoulder, for example within pocket 12. Once the desired weight shift or perturbation resistance is obtained, the weight placement (e.g., the amount of weight placed within each pocket and the corresponding weight-pocket location) may be recorded.

Anterior Balance Dysfunction.

To test for the appropriate weight placement for this dysfunction, a series of weights from ¼ to ½ pounds may be placed within any of pockets 15, 16, 19, 20, 23, 24, 25, or 26, and combinations thereof until the desired weight shift or perturbation resistance is achieved. The desired amount of weight shift or perturbation resistance will be that amount resulting in an acceptable level of improvement in balance and movement from the baseline observation and perturbation steps. Pockets 15, 16, 19, 20, 23, 24, 25, and 26 are on the back of vest 104 and a practical progression for weight placement may begin by placing weights on the top portion of the back of the vest and then proceeding downward. In some instances, it may be desirable (e.g., a quicker determination of proper weight placement may be made) to place weights first within one or more of pockets 15, 16, 19, and 20 before placing weights within other pockets, if necessary. Once the proper weight shift or perturbation resistance is obtained, the weight placement (e.g., the amount of weight placed within each pocket and the corresponding weight-pocket location) may be recorded.

Anterior Lateral Dysfunction to the Right.

For appropriate weight placement for this dysfunction, a series of weights from ¼ to ½ pounds may be placed within any of pockets 12, 14, 15, 18, 19, 22, 23, or 24, and combinations thereof until the desired weight shift or perturbation resistance is achieved. The desired amount of weight shift or perturbation resistance will be that amount resulting in an acceptable level of improvement in balance and movement from the baseline observation and perturbation steps. Pockets 12, 14, 15, 18, 19, 22, 23, and 24 are on the back of vest 104, and I have found that beginning weight placement in the upper left portion of the back of the vest and proceeding downward, is a practical progression for this dysfunction. In some instances, it may be desirable (e.g., a quicker determination of proper weight placement may be made) if weight placement is first tried within pockets 14 or 18. Once the desired weight shift or perturbation resistance is obtained, the weight placement (e.g., the amount of weight placed within each pocket and the corresponding weight-pocket location) may be recorded.

Anterior Lateral Dysfunction to the Left.

To test for the appropriate weight placement for this dysfunction, a series of weights from ¼ to ½ pound of weight may be placed within pockets any of 13, 16, 17, 20, 21, 25, 26, or 27, and combinations thereof until the desired weight shift or perturbation resistance is achieved. The desired amount of weight shift or perturbation resistance will be that amount resulting in an acceptable level of improvement in balance and movement from the baseline observation and perturbation steps. Pockets 13, 16, 17, 20, 21, 25, 26, and 27 are located on the back of vest 104 and I have found that a practical progression for selectively weighting for this dysfunction begins at the top right of the back of the vest and proceeds downward. In some instances it may be desirable (e.g., a quicker determination of proper weight placement may be made) if weight placement is first tried within pockets 17 or 21. Once the desired weight shift or perturbation resistance is obtained, the weight placement (e.g., the amount of weight placed within each pocket and the corresponding weight-pocket location) may be recorded.

Evaluation of proper weight placement may continue as long as necessary to determine whether the patient maintains their COG over their base of support for extended periods. The process to determine proper weight placement is typically iterative and based on trial and observation techniques. That is, after each incremental weight addition, it is often desirable to retest the patient using the perturbation and observation steps described above. In this way, a more accurate assessment of the effect of weight placement on the patient's balance and postural stability may be made.

If treatment is a success 106, then the process of assessing the need for a selectively weighted garment and determining proper weight placement throughout a patient's torso, is at its end 110. As described above, a determination of success is typically based on a comparison of the patient's ability to balance and move before and after the weighting treatment or assessment has begun, and at each step during the weighting process. That is, the patient's improvement is continually monitored from their baseline position (the baseline position being the assessment of the patient after observation step 100 and, optionally, perturbation step 116). The number of treatment trials necessary to reach success is highly variable. For example, the number of treatment trials necessary is often dependent on factors such as, the severity of the dysfunction (e.g., is the dysfunction in only one plane of movement, etc), and the patient's inability to attain or maintain COG over the base of support.

If the treatment is not successful, in that significant further improvement may be had, the treatment may be further checked 108. This typically involves altering the weight placement or overall weight amount. Lighter weights are typically used with smaller, lighter, or weaker individuals. Heavier weights are typically used with larger individuals or those with a greater inability to attain or maintain COG over the base of support. In addition, observation step 100 and perturbation step 116 may be repeated as necessary to further assess the most beneficial weight placement treatment.

When the weighting is successful, the patient's gait may be evaluated in order to assess whether their ambulation, or ability to walk, has improved. The patient may also be asked whether the weight is comfortable to them in order to determine whether any weight adjustments may be necessary. Typically, it is desirable to provide the individual with as little weight as possible while still ensuring that their COG remains over their base of support.

If any further attempt at weight adjustment produces no improvement, the treatment is successful 112, and is at its end 110. If not, there may be a further determination that all treatments have been tried. This typically involves rechecking weight placement and overall weight amount, as well as making use of the perturbation and visual techniques described above. If all selective weighting treatments have been tried, then the selective weighting and the outcome is still unsuccessful, selective weighting may simply be inappropriate for the patient and the assessment process is at its end 110. If not, the selective weighting treatment regime 104 is begun anew, and repeated.

The above method for determining proper weight placement may be performed manually, with use of a computer, or by some combination of the two. The use of a computer for accepting output signals from a force sensor and for calculating the COG by the subject may be highly desirable. For example, a patient may stand on a support surface or force plate connected to a computer and the computer may receive the patient's output, calculate their current COG, and develop the patient's baseline COG position. One acceptable example of such a system is found in U.S. Pat. No. 5,476,103 to Nahsner filed on Jun. 8, 1993 and entitled, "Apparatus and method for assessment and biofeedback training of leg coordination and strength skills," which is hereby incorporated by reference in its entirety. Other common examples of acceptable computers or processors for use with the present invention are known in the industry.

Figure 3A:
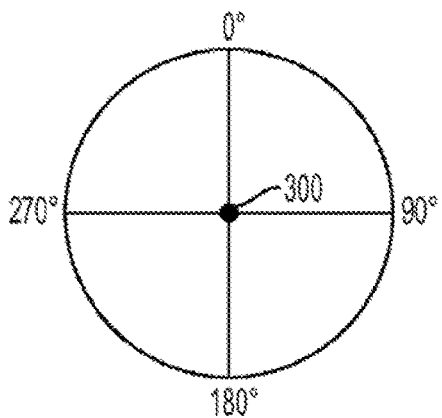
FIGS. 3A through 3C illustrate a computer assisted weighted method.
Figure 3B:
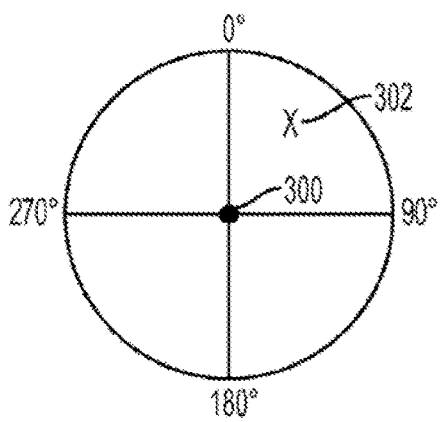
Figure 3C:
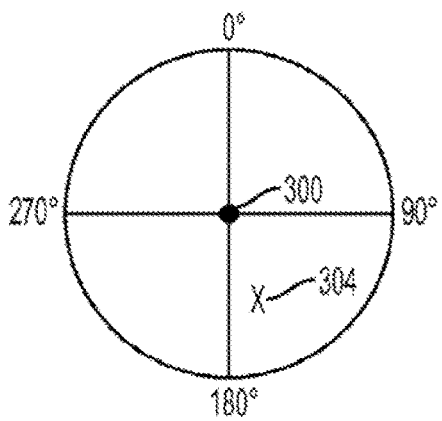

FIGS. 3A through 3C show a procedure for using a computer or processor to measure and facilitate COG correction via proper weight placement. As illustrated in FIG. 3A, position 300 indicates a patient's coordinate system when their COG is aligned over their base of support. FIG. 3B shows one example of a patient's position who is offset from COG as indicated by mark 302. In FIG. 3B, mark 302 indicates that the patient stands anteriorly and laterally (initially at least). Lateral and slight posterior selective weighting may be employed to correct the deficiency and move the patient COG over their base of support.

The procedure described just above i.e., systematically and selectively weighting the orthotic to improve COG placement, may also be employed while the patient is standing on the force plate or support surface. As the amount of the weights and their placement are adjusted, the computer receives the new output and registers the feedback on a screen. Thus, as the patient becomes more centered, mark 302 will move closer to position 300. In this way, the provider will readily be able to determine whether, and to what extent, the weight placement has caused the patient's COG to move toward center. FIG. 3B shows another example of a patient who is off center. In this figure, mark 304 indicates that the patient stands posteriorly and thus the selective weighting procedure may be anteriorly. However, it should be noted that selective weighting does not always begin at a position opposite that of the dysfunction (e.g., weighting anteriorly for a patient who stands posteriorly). These weighting starting points are merely illustrative.

Once a patient has achieved improvement in COG over base of support, or ideally, achieved their optimal COG over base of support, their ability to receive and interpret somatosensory information, coordinate muscular contractions, and move with more stability may then optionally be tested. The use of a computer together with devices for measuring COG, e.g., a plurality of support surfaces or force plates, may greatly facilitate patient assessment and testing in a number of ways. For example, computer assistance may facilitate quicker determination of proper weight placement (e.g., as described above), as well as provide more detailed information regarding a number of different patient positions. These positions may include, but are not limited to sitting, standing (on one or both legs), bending, squatting, walking up stairs. In addition, computer assistance may help provide more detailed information on the patient's reaction while standing on compliant and non-compliant surfaces, such as floors, rugs, etc. In this way, the testing of proper weight placement may be rigorously evaluated while simulating any number of conditions.

My invention also provides weighted orthotics or garments. Proper weight placement and weight size or amount are first determined using the methods described above. Then custom garments or orthotics may then be made to accommodate the patient's individual needs. For example, the positioning of the weights and their actual weight values, may be recorded using the procedures noted above and mapped onto a garment or orthotic. Similarly, recordation of the actual weight values may help facilitate a reduction in the overall weight of the garment or orthotic by making use of ratios. Once the location of weights and their values are recorded, tests may be performed to determine if reduction of all or some weight values by a fraction would still produce beneficial results in improving balance. In this way, for example, the amount of each weight may be reduced by a fraction, such as ½, resulting in ½ weight reduction in each location. Ratios may also be used to facilitate a reduction in the size of each weight. For example, the size of each weight may be reduced by a fraction if beneficial results in improving balance are still obtained.

The garments or orthotics, functionally, may be of a form, size, shape, and thickness, in order to accommodate the patient's needs. For example, the orthotic may take the form of a weighted shoulder pad, a weighted belt, a weighted seating device to be used in combination with a wheelchair, e.g., a weighted vest or other garment that may be attached (e.g., using Velcro or magnets) to the back of a wheelchair seat to improve the patient's stability, a weighted attachment to a brassiere, or any other weighted orthotic. Similarly, the weighted garment may be a brassiere, tee shirt, body suit, vest, or any other garment to be worn. For example, desirable garments may be those specifically designed as undergarments, e.g., those typically worn substantially out of public view (depending of course, on taste) or intended to be worn underneath outer garments, such as shirts, blouses, and jackets. One variation specifically includes the undershirts, brassieres, girdles, or girdle-like garments mentioned elsewhere. Of course, such undergarments may be made of fabric that is comfortable against the skin. The garment may be self-fastenable (using, e.g., buttons, snaps, hook and latch fabric, such as Velcro, and magnets, etc.) or held to the torso using belts, bands, etc.

The weights for placement within any of the weighted apparatuses may be rigid or may be flexible. The weights may be made of any suitable material, and be able to accommodate any thickness. When the weighted apparatus is a body suit or brassiere, for example, the weighted material may be flexible, thin, and made of a hypoallergenic material. In this way the entire suit or brassiere may be made of the weighted material, having a weight distribution determined in accordance with the above methods. In other variations, the material itself may not be weighted, but may incorporate weights therein. Any suitable type of weight may be used. For example, in one variation, flexible weights are used, of the type described in U.S. Pat. No. 6,005,041 to Cook filed on Nov. 9, 1995 and entitled "Reinforced Thermoplastic Elastomeric Gel (RTEG)," which is hereby incorporated by reference in its entirety.

In other variations, the weights are provided in packets having at least one hook and latch fabric, magnetic, or other easily attachable surface or portion. For example, the weight packet 204 shown in FIG. 2B may include an attachable surface or portion. In this way, the weights themselves may be attached to the apparel of the patient. For example, the weight packets may be attached to the waistline of a pair of paints, or may be attachable to a portion of a shirt, jacket, belt, etc.

I have found the weighted vest to be especially useful. The vest may have any number of optional panels, but typically may have a pair of front panels separated by a front, closing seam and a back panel or of course, it may be made up of: a front panel, a back panel, or side panels. The vest may be made of any number of suitable materials. The vest may be made of durable materials capable of withstanding the weight therein and capable of maintaining its integrity in the event the wearer falls. The vest may have any number of pockets or receptacles for receiving and securing the weights therein, as described above. Alternatively, the vest may have no pockets or receptacles and be manufactured in accordance with the above methods, wherein predetermination of the proper weight distribution is made and the material of the vest is weighted in accordance therewith.

The vest may be of any length and shape to accommodate the wearer's height, size, body type, comfort, and ability to maneuver about while wearing it. Similarly, the vest may be of any thickness so that it may be worn in any number of ways. For example, in one variation, the vest is relatively thin so that it may be worn underneath the wearer's clothing. In other variations, the vest is thick and may be worn on top of the wearer's clothing.

Figure 4A:
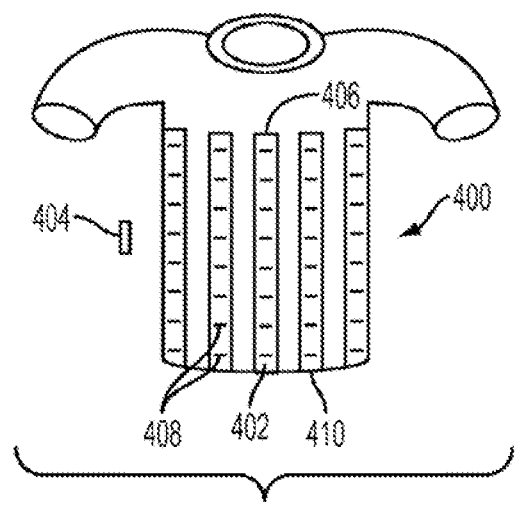
FIGS. 4A through 4C show a weighted shirt having longitudinal tubes for the introduction of weights.

Another weightable or weighted garment of particular usefulness is shown in FIG. 4A. The garment 400, although shown in the form of a shirt, may be a vest, corset, or other apparel, having at least a portion worn on the torso. Central to this garment 400 are the linear enclosures 402 that are adapted to receive weights in shapes and forms that may be inserted into the linear enclosures 402. Shown in FIG. 4A are linear enclosures 402 having an open upper end 406, cross-slits 408, and open lower and 410. Each of the linear enclosures 402 would typically have the openings specified just above.

Figure 4B:
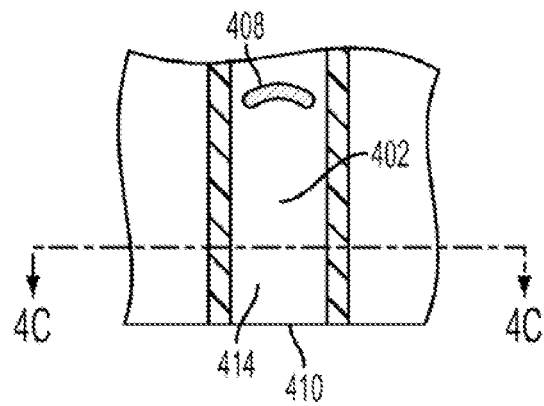
Figure 4C:
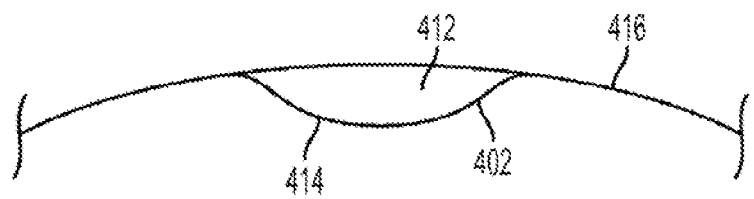

FIG. 4B shows a partial close-up view of one of the linear enclosures 402 with the open cross-slit 408 and the open bottom end 410. FIG. 4C shows a top view cutaway of a linear enclosure 402 and the open space 412 within for placement of an appropriate weight. The linear enclosure 402 shown in FIGS. 4B and 4C is made up of a cover 414 that is surged to the backing material 416.

I have found that constructing one or more of the cover 414 and the backing material 416 from a stretchable material such as Nylon, Lycra™, or the like, tends to hold the weights in position in the linear enclosures, particularly if the weights are resistant to movement after placement or covered with a rubber material. Returning to FIG. 4A, the linear enclosures 402 shown there are positioned longitudinally with the torso of the wearer. However, they need not be so. Other configurations, helical about the torso, of differing widths, as well as single enclosures having varying widths, are also suitable.

Figure 5A:
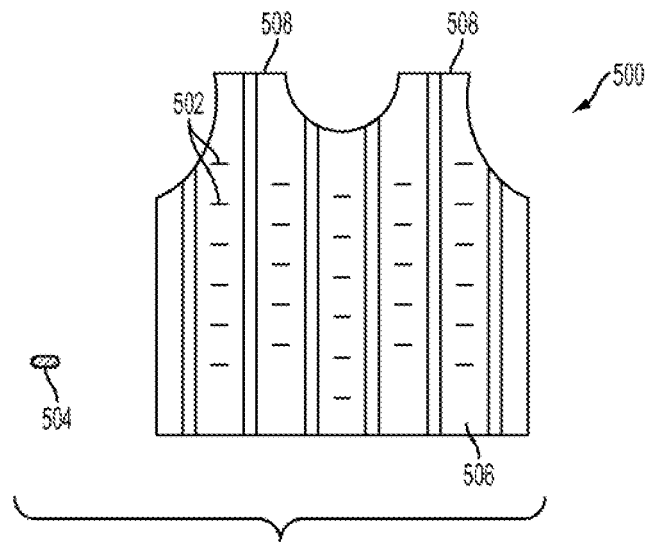
FIGS. 5A and 5B illustrate garments having slits for the introduction of weights.
Figure 5B:
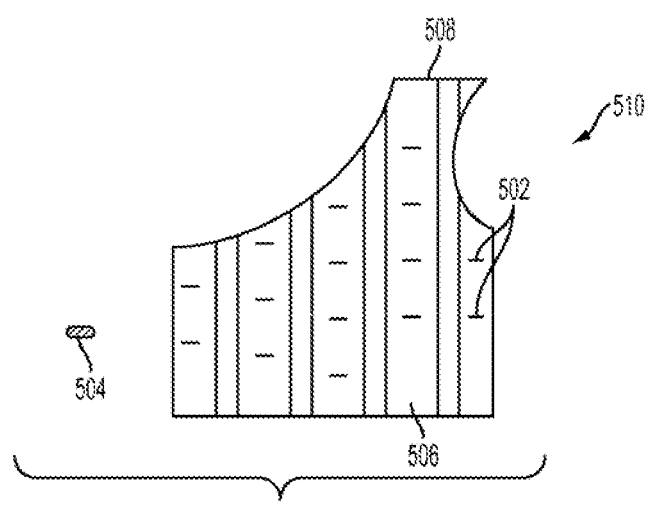
Figure 5C:
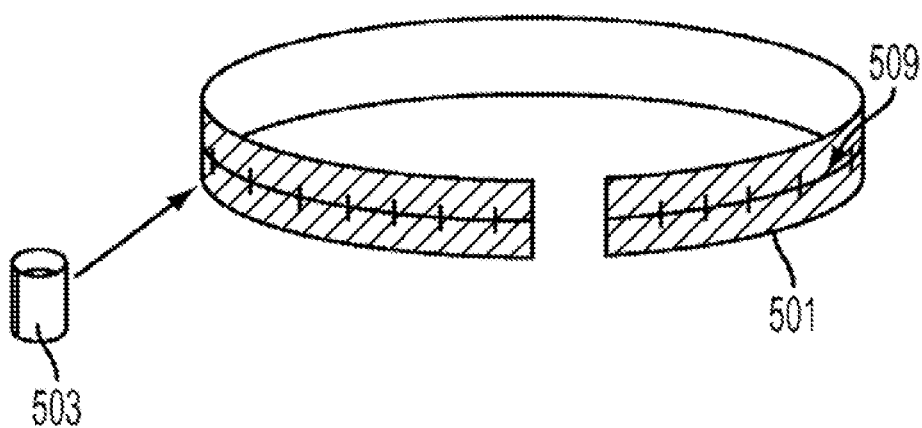
FIG. 5C illustrates a garment configured as a belt showing a weight packet that may be secured thereto.

Other useful weighted garments are illustrated in FIGS. 5A, 5B, and 5C. FIG. 5A illustrates a weighted garment 500 configured to be worn about both shoulders while FIG. 5B illustrates a weighted garment 510 configured to be worn about one shoulder. The garments 500 and 510 may be double layered for example, and be made of a breathable and stretchable material. Slits 502 are provided variously along the length of the garments for the introduction of weights 504. Slits for weights may also be provided on the shoulder portions of the garments 508. The weights 504 may be held in place, for example, by sewing the weights in place at or near slit 502 or the weights may be allowed to migrate to the base of the garment 506 before being sewn in place. In addition, any of the methods of attachment described above (e.g., hook and latch fabric, magnetism, etc.) may be employed here. In addition, while horizontal slits are represented here, the slits need not be so. Other configurations are also suitable. For example, FIG. 5C is another variation of an orthotic device configured as a belt 509, as described above. A weighted packet 503 may be positioned and secured to the inner, outer, or either side surface of the device 509 by any of the attachment mechanisms described. The orthotic device shown in FIG. 5C also illustrates markings 501 uniquely indicating the position of any attached weight packet 503, as described above.

Although illustrative variations of the present invention have been described above, it will be evident to one skilled in the art that various changes and modifications may be made without departing from the invention. For instance, variations of the present invention may include weighted devices on the lower extremities or any other area of the body. In addition, the present invention may include the use of the procedures described herein for therapy, repeating the procedures as often as necessary, as the amount or placement of the weights may change over time. It is intended in the following claims to cover all such changes and modifications falling within the true scope and spirit of the invention.

The invention claimed is:

1. A garment for improving a subject's ability to maintain a center of gravity over a base of support, comprising:
    a panel having a front and a back, wherein the front or back of the panel is configured as a hook or latch fabric; and
    at least one repositionable weight packet configured to hold at least one weight and to attach to the front or back of the panel,
    wherein a surface of the weight packet is a latch or hook fabric configured to attach the weight packet to the hook or latch fabric of the panel;
    wherein the panel has a plurality of immediately adjacent and continuous positions along a length of hook or latch fabric extending across substantially the entire panel, to which positions the repositionable weight packet is removably and selectively attached.

2. An apparatus comprising:
    a garment made of a flexible and wearable material to be worn by a subject, the garment capable of receiving one or more sources of stimuli originating from a weight over a plurality of immediately adjacent and continuous positions; and
    one or more repositionable sources of stimuli from a weight attached to the garment.

* * * * *